(12) United States Patent
Kim et al.

(10) Patent No.: US 8,702,748 B2
(45) Date of Patent: Apr. 22, 2014

(54) SMALL CALIBER LAPAROSCOPE SURGICAL APPARATUS

(75) Inventors: Dong Jun Kim, Goyang-si (KR); Jun Woo Park, Goyang-si (KR); Yung Ho Jo, Goyang-si (KR)

(73) Assignee: National Cancer Center, Gyeonggi-Do (KR)

( * ) Notice: Subject to any disclaimer, the term of this patent is extended or adjusted under 35 U.S.C. 154(b) by 219 days.

(21) Appl. No.: 12/738,478

(22) PCT Filed: Oct. 16, 2008

(86) PCT No.: PCT/KR2008/006112
§ 371 (c)(1),
(2), (4) Date: Jul. 16, 2010

(87) PCT Pub. No.: WO2009/051418
PCT Pub. Date: Apr. 23, 2009

(65) Prior Publication Data
US 2010/0280543 A1    Nov. 4, 2010

(30) Foreign Application Priority Data
Oct. 17, 2007  (KR) .................. 10-2007-0104642

(51) Int. Cl.
*A61B 17/00*    (2006.01)
(52) U.S. Cl.
USPC ...................... 606/205; 606/206; 606/207
(58) Field of Classification Search
CPC ............................................. A61B 2019/2942
See application file for complete search history.

(56) References Cited

U.S. PATENT DOCUMENTS

| 4,503,842 | A |   | 3/1985 | Takayama |
| 4,834,069 | A |   | 5/1989 | Umeda |
| 5,752,973 | A | * | 5/1998 | Kieturakis ............... 606/207 |
| 5,904,702 | A | * | 5/1999 | Ek et al. ................. 606/206 |
| 6,206,903 | B1 | * | 3/2001 | Ramans ................... 606/205 |
| 6,817,974 | B2 | * | 11/2004 | Cooper et al. ............ 606/205 |
| 7,101,363 | B2 | * | 9/2006 | Nishizawa et al. ........ 606/1 |

(Continued)

FOREIGN PATENT DOCUMENTS

| EP | 1 836 986 A2 | 9/2007 |
| JP | 08-038495 | 2/1996 |

(Continued)

OTHER PUBLICATIONS

Supplemental European Search Report, EP 08 83 9041, Mailed Nov. 4, 2010.

*Primary Examiner* — Darwin Erezo
*Assistant Examiner* — Kendra Obu
(74) *Attorney, Agent, or Firm* — Seed IP Law Group PLLC

(57) ABSTRACT

A laparoscopic surgical instrument includes a shaft and a head having a distal end to which a variety of surgical instruments are attached. The laparoscopic surgical instrument also includes a flexible joint installed between the shaft and the head; a longitudinal-driving unit including a longitudinal-driving wire connected with both longitudinal ends of the head and a longitudinal-driving roller turning the longitudinal-driving wire and a transverse-driving unit including a transverse-driving wire connected with both transverse ends of the head and a transverse-driving roller turning the transverse-driving wire. The longitudinal-driving unit turns the flexible joint in the longitudinal direction, the transverse-driving unit turns the flexible joint in the transverse direction, and the shaft has a small diameter.

10 Claims, 13 Drawing Sheets

(56) References Cited

U.S. PATENT DOCUMENTS

| | | | |
|---|---|---|---|
| 7,686,826 B2 * | 3/2010 | Lee et al. | 606/205 |
| 2003/0135204 A1 * | 7/2003 | Lee et al. | 606/1 |
| 2004/0236316 A1 | 11/2004 | Danitz et al. | |
| 2009/0112230 A1 * | 4/2009 | Jinno | 606/130 |

FOREIGN PATENT DOCUMENTS

| | | |
|---|---|---|
| JP | 08-224241 | 9/1996 |
| JP | 09-276283 | 10/1997 |
| JP | 2003-061969 | 3/2003 |
| JP | 2005-505314 | 2/2005 |
| JP | 2006-061364 | 3/2006 |
| KR | 1020050100147 A | 10/2005 |
| KR | 1020050102536 A | 10/2005 |
| KR | 1020060134840 A | 12/2006 |
| KR | 1020070079052 A | 8/2007 |
| WO | WO 02/087420 A2 | 11/2002 |

* cited by examiner

SMALL CALIBER LAPAROSCOPE SURGICAL APPARATUS

This application is the U.S. National Stage of International Application No. PCT/KR2008/006112, filed 16 Oct. 2008, which designates the U.S., published in English, and claims priority under 35 U.S.C. §§119 or 365(c) to Korean Application No. 10-2007-0104642, filed 17 Oct. 2007. The entire teachings of the above applications are incorporated herein by reference.

TECHNICAL FIELD

The present invention relates to a laparoscopic surgical instrument used for laparoscopic surgery, and more particularly, to a laparoscopic surgical instrument having a small diameter shaft, wherein a flexible joint is installed between a shaft and a head of the laparoscopic surgical instrument, thereby freely rotating the head.

BACKGROUND ART

Laparoscopic surgery is a surgical procedure in which a small incision of approximately one centimeter is made around the navel, through which an endoscope (laparoscope) and several surgical instruments are inserted to perform surgical procedures. In contrast to open abdominal surgery, laparoscopic surgery usually involves less pain, less scarring, and reduced recovery time after the operation since laparoscopic surgery only needs one or more small incisions to be made in the abdomen. Because of these advantages, the use of laparoscopic surgery as a popular diagnostic and treatment tool for a variety of diseases has increased.

Laparoscopic surgery can be directly performed with surgical instruments or be done with small robotic arms by surgeons. An example of a robot-assisted laparoscopic surgery is disclosed in Korean Patent No. 10-0585458, and the surgeon guides the movement of slave robotic arms and surgical instruments by manipulating a master robot.

During a robot-assisted laparoscopic surgery, the surgeon can perform the surgery at a console several feet away from a patient. Further, the robot-assisted laparoscopic surgery can be done in the same way the experienced surgeon does, even though the surgeon is not at the operating table.

Since the surgeons experience less physical and mental fatigue during laparoscopic surgery compared to open abdominal surgery during a surgical operation, they can as a result take care of more patients.

In laparoscopic surgery, the endoscope (laparoscope) and more than two surgical instruments are basically used. The endoscope is used to provide images of the internal organs for the surgeon to see. As the surgical instruments are special tools and devices provided for a surgical operation, grasping forceps are normally attached to the head of the instrument and are used to block blood vessels and to suture tissues.

The surgical instruments need to be made in a minimal size in order to minimize invasive damage to the body of the patient. For an accurate surgical operation of internal organs, a joint can be formed between a shaft and a head portion of the surgical instrument so that the head portion can rotate within a certain angle. An example of the surgical instrument formed with the joint is disclosed in Korean Patent No. 10-2006-0056238. In this prior art, the joint actuated by a gear is installed between the head and shaft.

In the surgical instrument having a joint actuated by a gear between the shaft and the head, there is a limit in making the diameters of the shaft and the head smaller attributable to the size of the gear. Further, there have been problems with the development and the production of the instrument because of the complicated driving means to manipulate and actuate the gear in the joint.

In laparoscopic surgery with the surgical instrument having the joint between the shaft and the head, the surgical operation can be done with minimized incisions in the abdomen. However, as the sizes of the shaft and the head become bigger due to the size of the joint, the incision needs to become bigger such that the shaft can be inserted into the patient's abdomen.

Besides, the joint actuated by the gear can rotate the head by certain degrees at regular intervals depending on the gear ratio, and thus the head cannot rotate as much as the clinician wants.

Further, only one joint actuated by the gear is not enough to rotate the head in all directions and more than two joints are needed to resolve this problem. In this case, in order to move the joints, the devices become complicated and the diameter of the shaft needs to be bigger, as a result raising the cost of manufacturing the surgical instruments.

DISCLOSURE OF INVENTION

Technical Problem

The present invention has been proposed to solve the aforementioned problems and embodiments of the present invention provide a joint rotating in multiple degrees of freedom between a shaft and a head of a laparoscopic surgical instrument in order to improve the rotating range of the head.

Embodiments of the present invention also provide a laparoscopic surgical instrument having a small diameter shaft in order to minimize the incision on the body of the patient made during surgical operations.

Technical Solution

In an exemplary embodiment of the present invention, the laparoscopic surgical instrument includes a shaft and a head having a distal end to which a variety of surgical instruments are attached. The laparoscopic surgical instrument may include a flexible joint installed between the shaft and the head; a longitudinal-driving unit including a longitudinal-driving wire connected with both longitudinal ends of the head and a longitudinal-driving roller turning the longitudinal-driving wire, wherein the longitudinal-driving unit turns the flexible joint in the longitudinal direction; and a transverse-driving unit including a transverse-driving wire connected with both transverse ends of the head and a transverse-driving roller turning the transverse-driving wire, wherein the transverse-driving unit turns the flexible joint in the transverse direction, wherein the shaft has a small diameter.

The longitudinal-driving wire of the longitudinal-driving unit is partially wound on the longitudinal-driving roller, the transverse-driving wire of the transverse-driving unit is partially wound on the transverse-driving roller, and both ends of the longitudinal-driving wire and the transverse-driving wire are inserted into the shaft and extend through outside of the flexible joint so as to be connected with the head.

The flexible joint includes a plurality of rings arranged in a row.

The plurality of rings includes small rings and large rings arranged in a row to repeatedly cross each other.

The small rings and the large rings are made of elastic material.

Each of the large rings has guide grooves on outer portions thereof such that the longitudinal-driving wire and the transverse-driving wire are linearly inserted into the guide grooves.

The guide grooves are arranged in the exterior circumferential portions of the large ring at 90 degree intervals.

The laparoscopic surgical instrument may further include an outer cover attached to an outside of the flexible joint so as to prevent the longitudinal-driving wire and the transverse-driving wire from moving out of the guide grooves of the large rings.

The laparoscopic surgical instrument may further include a steel wire that is repeatedly wound into a coil shape with an equal diameter.

The laparoscopic surgical instrument may further include forceps included or connected to the head. The forceps include a 2 forcep jaws separated to top and bottom sides and rotatably attached to the head; a driving roller rotating the forceps; and a forceps-driving unit actuating the driving roller to turn the forceps.

Each of the forcep jaws has a guide slit formed inside thereof. The driving roller is rotatably coupled with the body connected with the head and has driving pins formed on both sides, each of the driving pins connected with the guide slit of each of the forcep jaws.

The forceps-driving unit includes a forceps-driving wire inserted through the shaft, the flexible joint and a through-hole of the head, and having a folded portion wound on an exterior circumference of the driving roller; a forceps-driving roller provided on an upper portion of the shaft such that a terminal portion of the forceps-driving wire is wound thereon; and a forceps-driving motor turning the forceps-driving roller.

Advantageous Effects

In the exemplary embodiment of the present invention, the laparoscopic surgical instrument is provided with the flexible joint between the shaft and the head, a flexible joint which can be made smaller and simpler with lower production cost compared to the gear-type joint in the prior art, and a shaft and a head which can be made in a small diameter.

The flexible joint of the laparoscopic surgical instrument having a small diameter shaft in accordance with the present invention can be more precisely controlled compared to the gear-type joint actuated by the gear in the prior art.

In addition, since the laparoscopic surgical instrument of the present invention is equipped with the shaft and the head having small diameters, invasive damage to the body of the patient can be minimized, thereby reducing post-surgery recovery time.

BEST MODE FOR CARRYING OUT THE INVENTION

The features and other advantages of the present invention will be more clearly understood from the following detailed description taken in conjunction with the accompanying drawings. Hereinafter, a laparoscopic surgical instrument having a small diameter shaft will be described more in detail with reference to the accompanying drawings in accordance with the preferred embodiments of the present invention.

Figure 1:
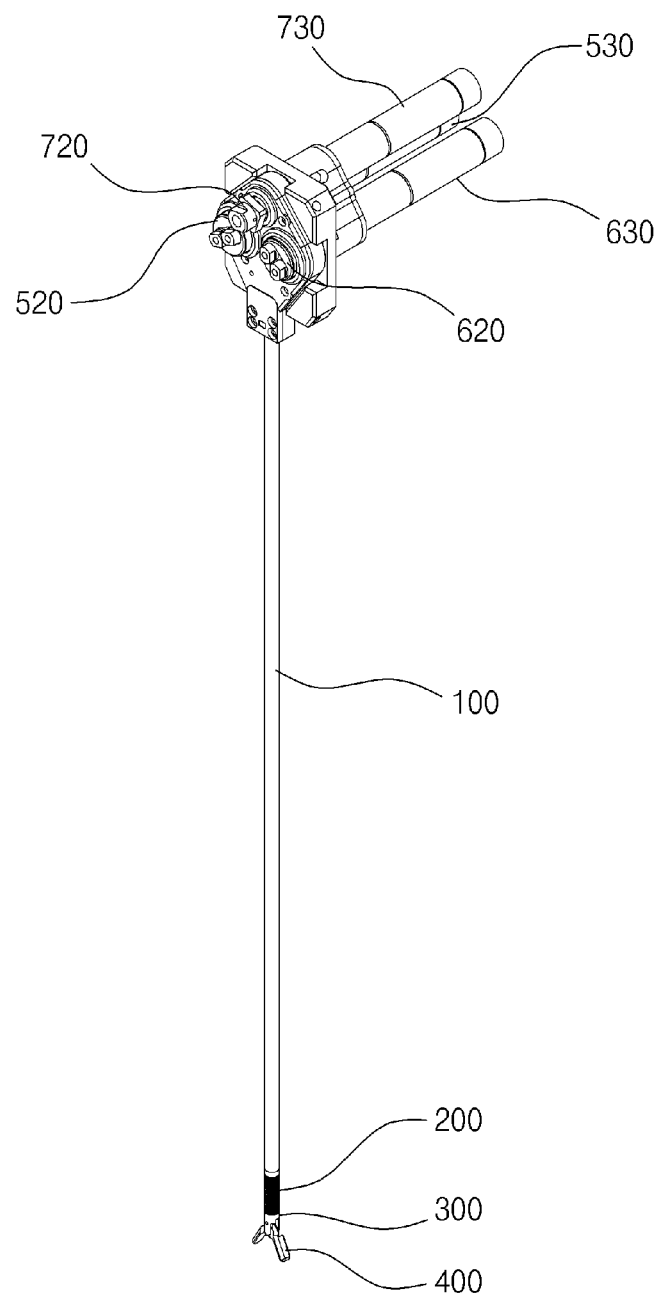
FIG. 1 is a perspective view illustrating a laparoscopic surgical instrument having a small diameter shaft in accordance with an embodiment of the present invention.
Figure 2:
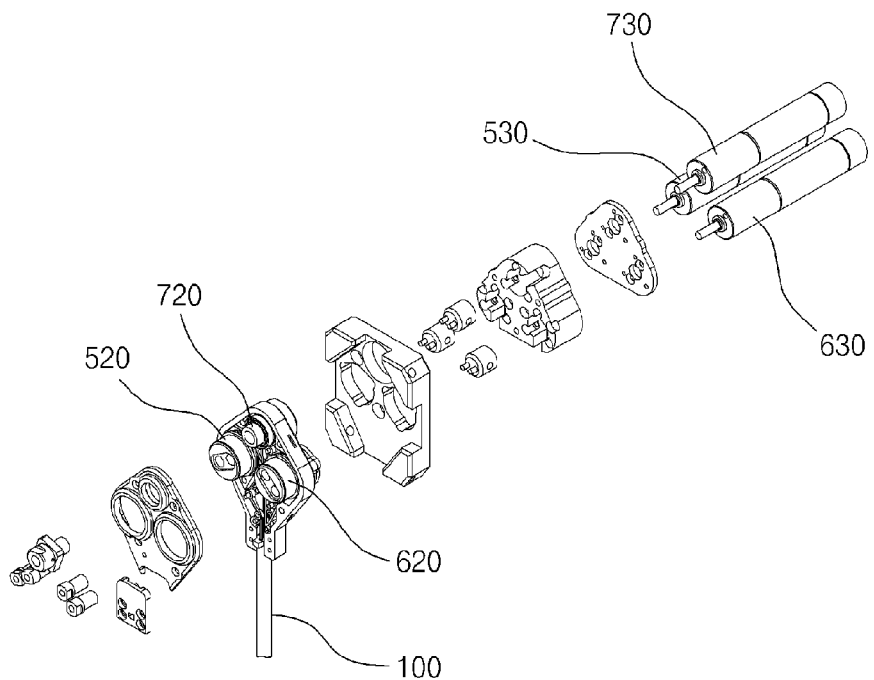
FIG. 2 is an exploded perspective view illustrating the driving unit of the laparoscopic surgical instrument of FIG. 1.
Figure 3:
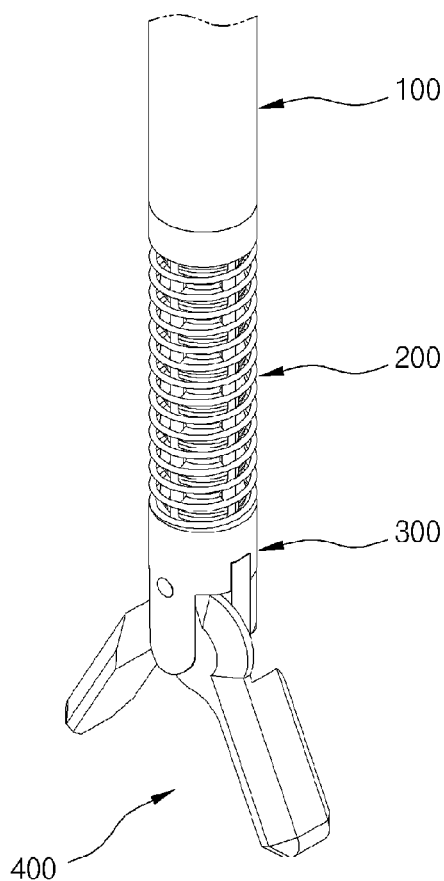
FIG. 3 is an exploded perspective view illustrating the flexible joint, the head and the forceps of the laparoscopic surgical instrument of FIG. 1.

Referring to FIGS. 1 to 3, the laparoscopic surgical instrument having a small diameter shaft includes an elongated shaft 100 inserted into an incision in the abdomen; a flexible joint 200 connected with the distal portion of the shaft 100; a head 300 connected with the bottom portion of the flexible joint 200; forceps 400 (a surgical instrument) installed at the bottom portion of the head 300; and drive portions 500, 600 and 700 each of which actuates a respective one of the flexible joint 200 and the forceps 400.

The shaft 100 is inserted into the operation region during the surgical operation, formed as an elongated shape with a hollow tube inside, and both ends of the shaft 100 are opened.

Figure 4:
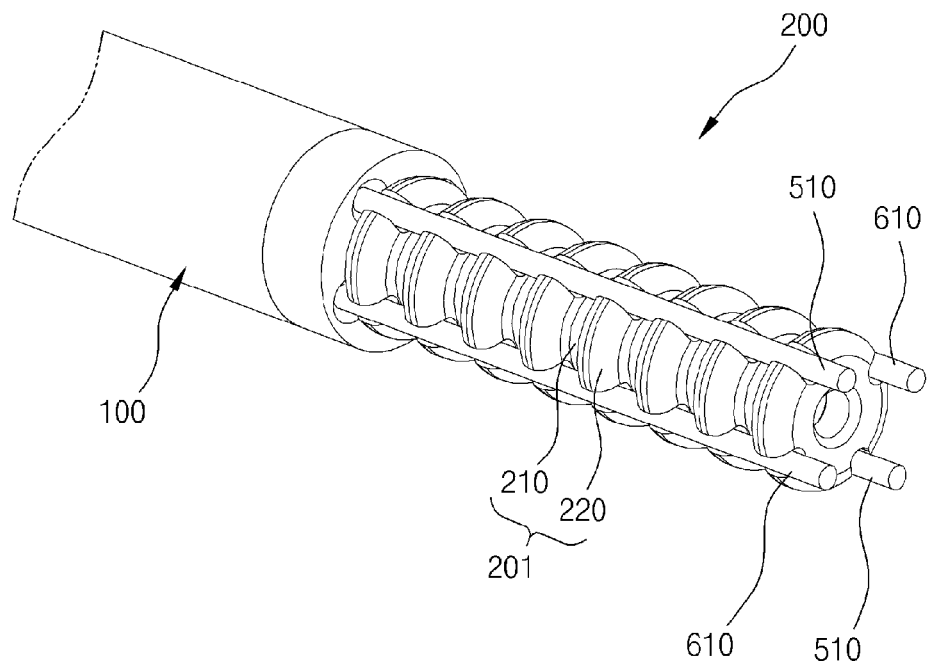
FIG. 4 is an enlarged perspective view of the flexible joint of FIG. 1.
Figure 5:
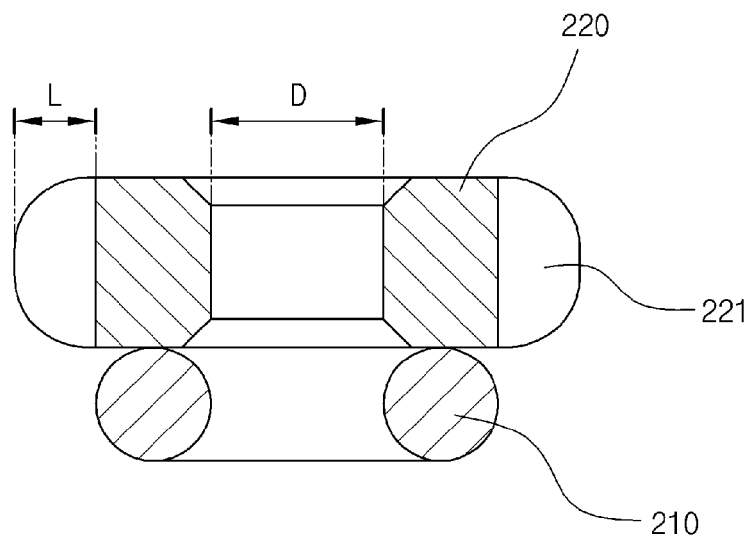
FIG. 5 is a cross-sectional view illustrating the small ring and the large ring of the flexible joint of FIG. 4 in detail.
Figure 6:
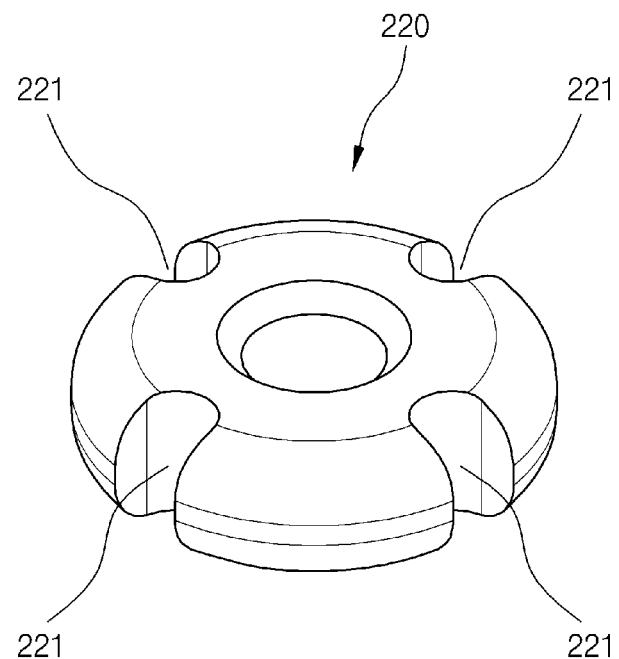
FIG. 6 is an enlarged perspective view of the large ring of FIG. 5.

Referring to FIGS. 4 to 6, the flexible joint 200 is structured with a plurality of rings 201 arranged in a row. Each of the rings 201 consists of a small ring 210 and a large ring 220. Both the small and large rings 210 and 220 have the same internal diameter "D." The reason is that a strait hollow with a uniform diameter can be formed inside the flexible joint 200 such that the wires or power lines can pass through the straight hollow. Each of the large rings 220 is provided with guide grooves 221 for inserting a longitudinal-driving wire 510 and a transverse-driving wire 610 which will be described below in four portions of the exterior circumference thereof. The guide grooves 221 are formed in the exterior circumference of the large ring at 90 degrees intervals. The large rings 220 can be preferably manufactured larger than the small rings 210 by the depth "L" of the guide grooves 221.

The rings 201 of the flexible joint 200 can be made of hard material such as steel or soft material with elasticity such as rubber.

The flexible joint 200 configured as aforementioned is connected at the top portion thereof with the shaft 100 and at the bottom portion thereof with the head 300, respectively.

Figure 7:
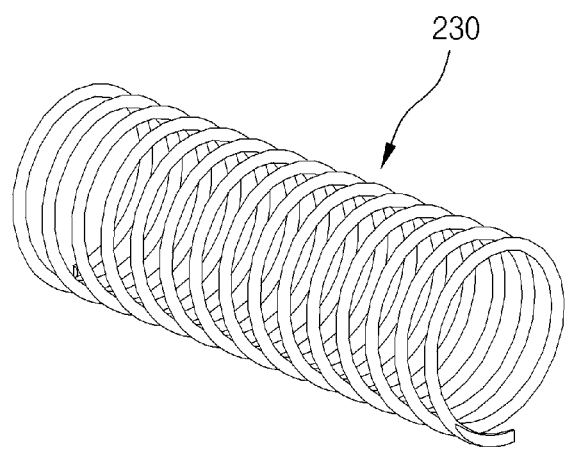
FIG. 7 is an enlarged perspective view of the outer cover of the flexible joint of FIG. 4.

Referring to FIGS. 4 and 7, the flexible joint 200 is covered with a coil-shaped outer cover 230, which is formed by repeatedly winding a steel wire in the same diameter. The outer cover 230 prevents the longitudinal-driving wire 510 and the transverse-driving wire 610 from moving out of the guide grooves 221 of the large rings 220 when the flexible joint 200 is bending.

The outer cover 230 is illustrated and described as a coil-shaped figure as above. However, the present invention is not restricted to the above-described figure, and the outer cover 230 can be made of a hose which cannot expand and contract in a circle direction while expanding and contracting in the longitudinal direction. For this hose, an accordion-shaped hose or a flexible style pipe can be used.

Figure 8:
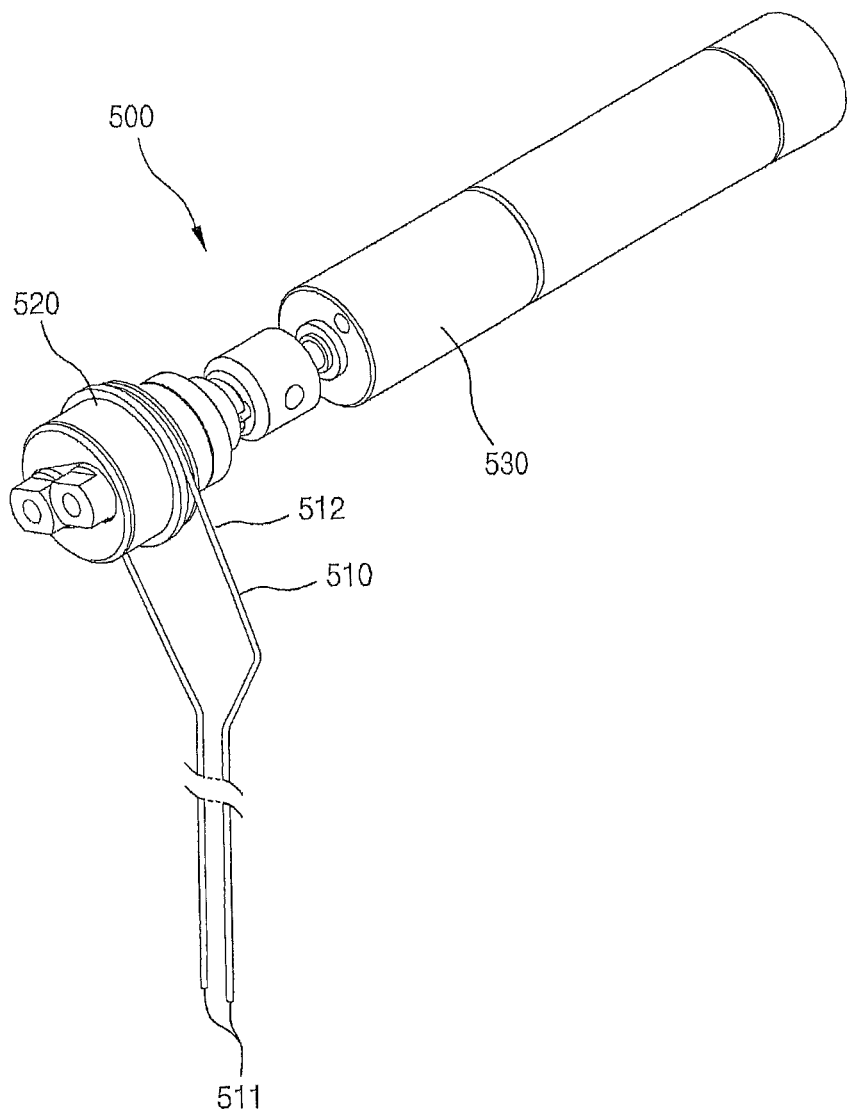
FIG. 8 is an enlarged perspective view of the longitudinal-driving unit of the laparoscopic surgical instrument having a small diameter shaft in accordance with an embodiment of the present invention.
Figure 14:
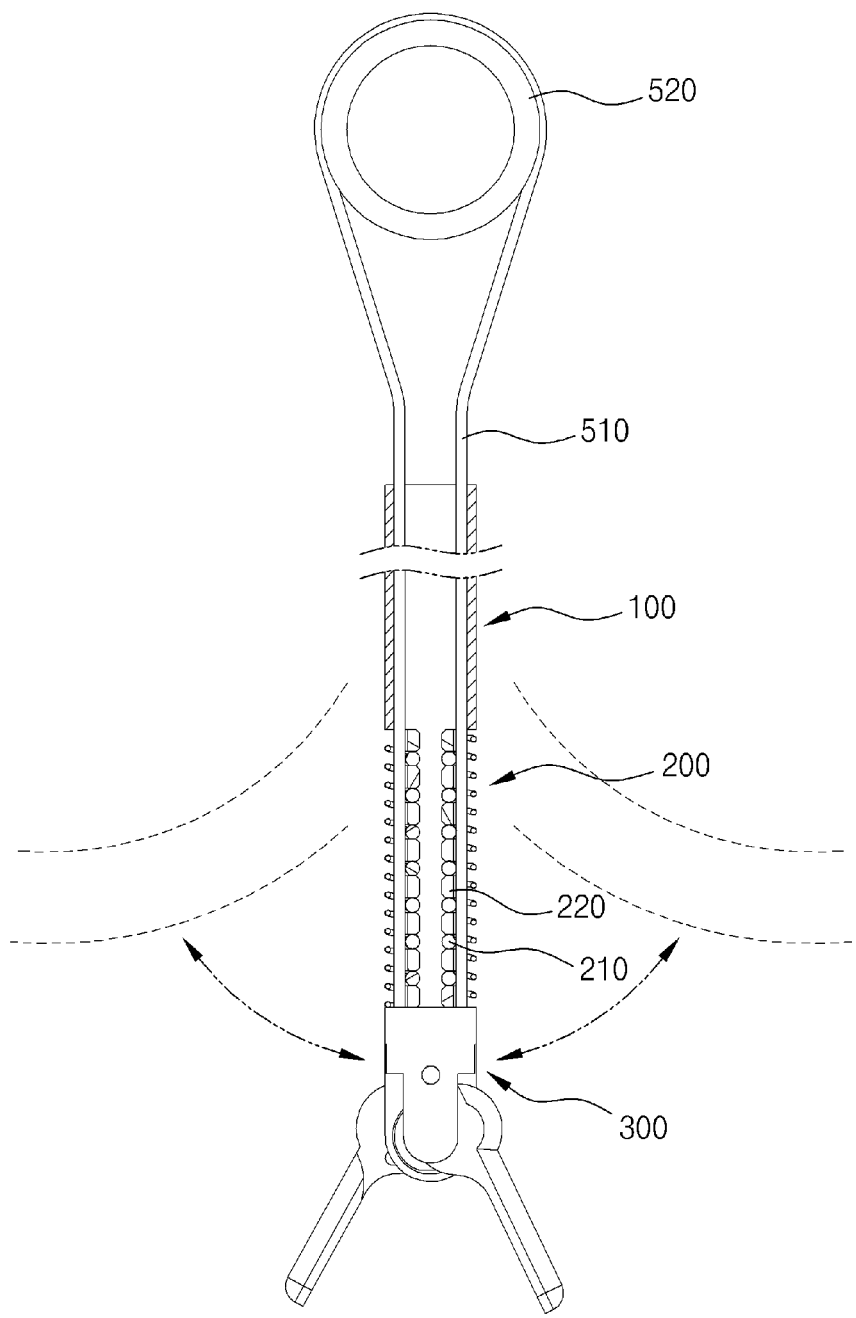
FIG. 14 is a perspective view showing the operating status of the laparoscopic surgical instrument having a small diameter shaft in accordance with an embodiment of the present invention, in which the head is longitudinally driven by the longitudinal-driving unit.

Referring to FIGS. 8 and 14, the longitudinal-driving unit 500 actuates the flexible joint 200 to fold in the longitudinal direction of the head 300, and includes the longitudinal-driving wire 510, a longitudinal-driving roller 520, and a longitudinal-driving motor 530.

The longitudinal-driving wire 510 is implemented with one wire. The longitudinal-driving wire 510 is bent in such a fashion that opposite terminal portions 511 join in one direction, and then the distal ends thereof where the terminal portions 511 are located are inserted into the distal end of the shaft 100. The longitudinal-driving wire 510 inserted into the shaft 100 is linearly inserted into two longitudinally-directed groove sets of the guide grooves 221 (see FIG. 6) of the large rings 220 in the flexible joint 200, and both terminal portions 511 are connected with both longitudinally-directed connecting ends of the head 300. A joining portion 512 of the longitudinally-drive wire 510 is located on the top portion (proximal portion) of the shaft 100 and is wound on the longitudinal-driving roller 520 connected with the longitudinal-driving motor 530. Preferably, the longitudinal-driving wire 510 can be wound so as to be rotatable in both directions of the longitudinal-driving roller 520.

The longitudinal-driving wire 510 wound on the longitudinal-driving roller 520 moves in the direction where the longitudinal-driving roller 520 rotates. When the longitudinal-driving roller 520 rotates in the right direction, the right side terminal portion 511 of the longitudinal-driving wire 510 comes out and the opposing left side terminal portion 511 is inserted therein.

Figure 9:
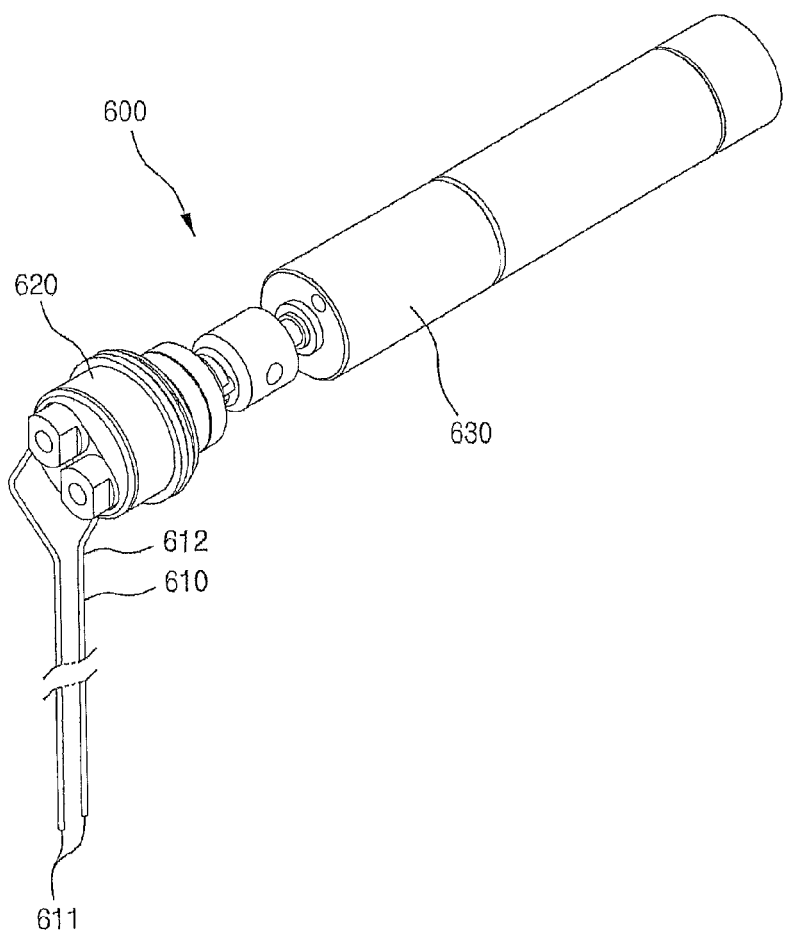
FIG. 9 is an enlarged perspective view of the transverse-driving unit of the laparoscopic surgical instrument having a small diameter shaft.
Figure 15:
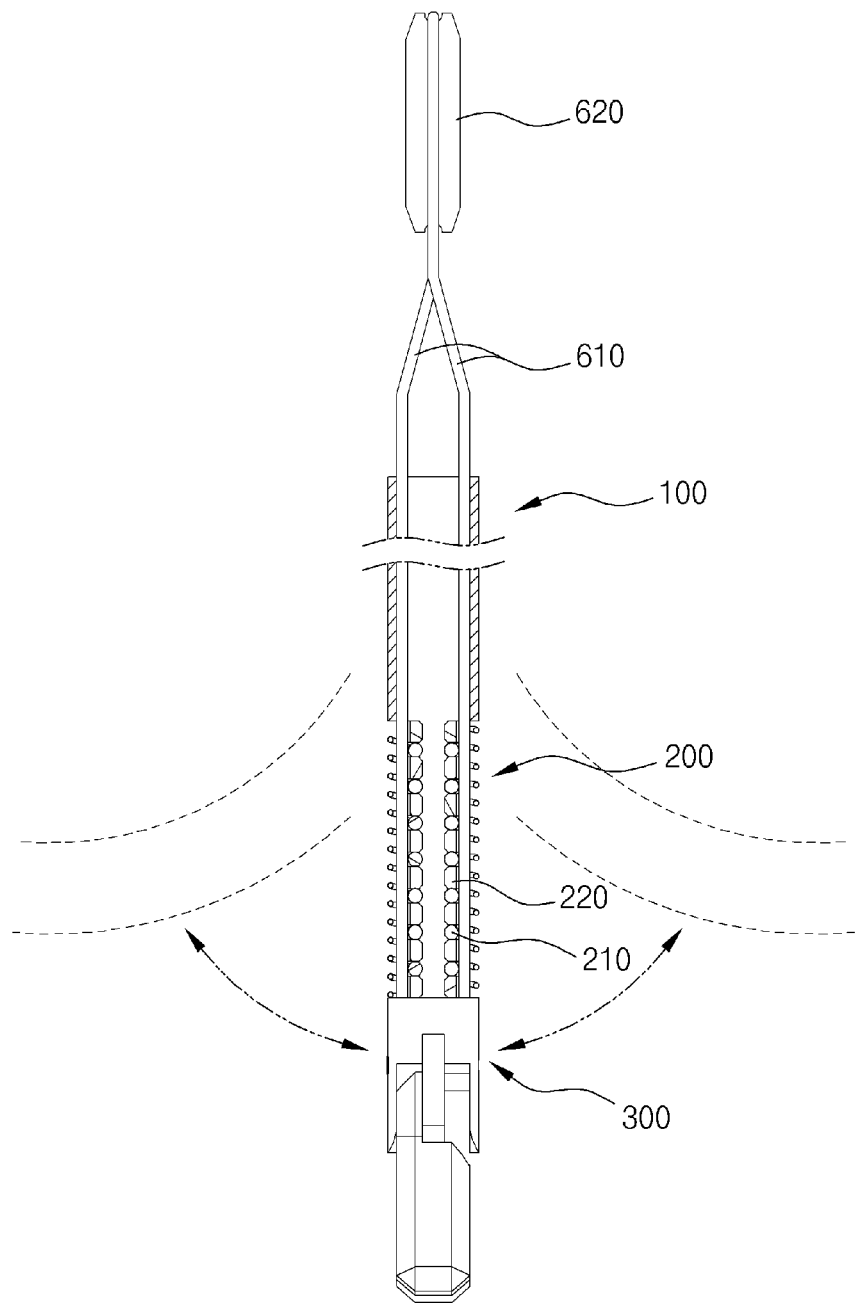
FIG. 15 is a perspective view showing the operating status of the laparoscopic surgical instrument having a small diameter shaft in accordance with an embodiment of the present invention, in which the head is transversely driven by the transverse-driving unit.

Referring to FIGS. 9 and 15, the transverse-driving unit 600 actuates the flexible joint 200 to fold in the transverse direction of the head 300, and includes the transverse-driving wire 610, the transverse-driving roller 620, and the transverse-driving motor 630.

Referring to the transverse-driving unit 600 configured as above, the transverse-driving wire 610 is implemented with one wire like the longitudinal-driving wire 510 (see FIG. 8). The transverse-driving wire 610 is bent in such a fashion that opposite terminal portions 611 join in one direction, and then the distal ends thereof where the terminal portions 611 are located are inserted into the distal end of the shaft 100. The transverse-driving wire 610 inserted into the shaft 100 is inserted linearly into the two transversely-directed guide grooves (refer to 221 of FIG. 6) among the guide grooves 221 of the large rings 220 in the flexible joint 200, and both the terminal portions 611 are connected with both transversely-directed connecting ends of the head 300. The joint portion 612 of the transverse-driving wire 610 is located on the top portion (proximal portion) of the shaft 100 and is wound on the transverse-driving roller 620 connected with the transverse-driving motor 630.

The transverse-driving wire 610 wound on the transverse-driving roller 620 is moving in the direction where the transverse-driving roller 520 rotates. When the transverse-driving roller 620 rotates in the right direction based on the shaft 100, the right side terminal portion 611 of the transverse-driving wire 610 comes out and the opposing left side terminal portion 611 is inserted therein.

Figure 10:
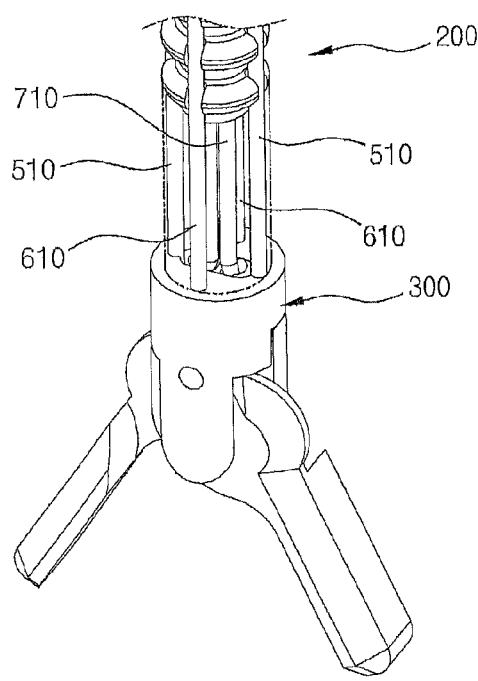
FIG. 10 is an enlarged perspective view illustrating the assembled state of the head of FIG. 3 with the flexible joint, the longitudinal-driving wire, and the transverse-driving wire.

Referring to FIG. 10, the head 300 has the same external diameter as the shaft (refer to 100 of FIG. 1) and is attached to the distal bottom end of the flexible joint 200. Both the terminal portions 511 of the longitudinal-driving wire 510 and both the terminal portions 611 of the transverse-driving wire 610 are attached to both sides of the connecting surfaces in the longitudinal direction and on both sides of the connecting surfaces in the transverse direction, respectively. On the distal bottom end of the head 300, a variety of surgical instruments are attached or constructed as one body.

Figure 11:
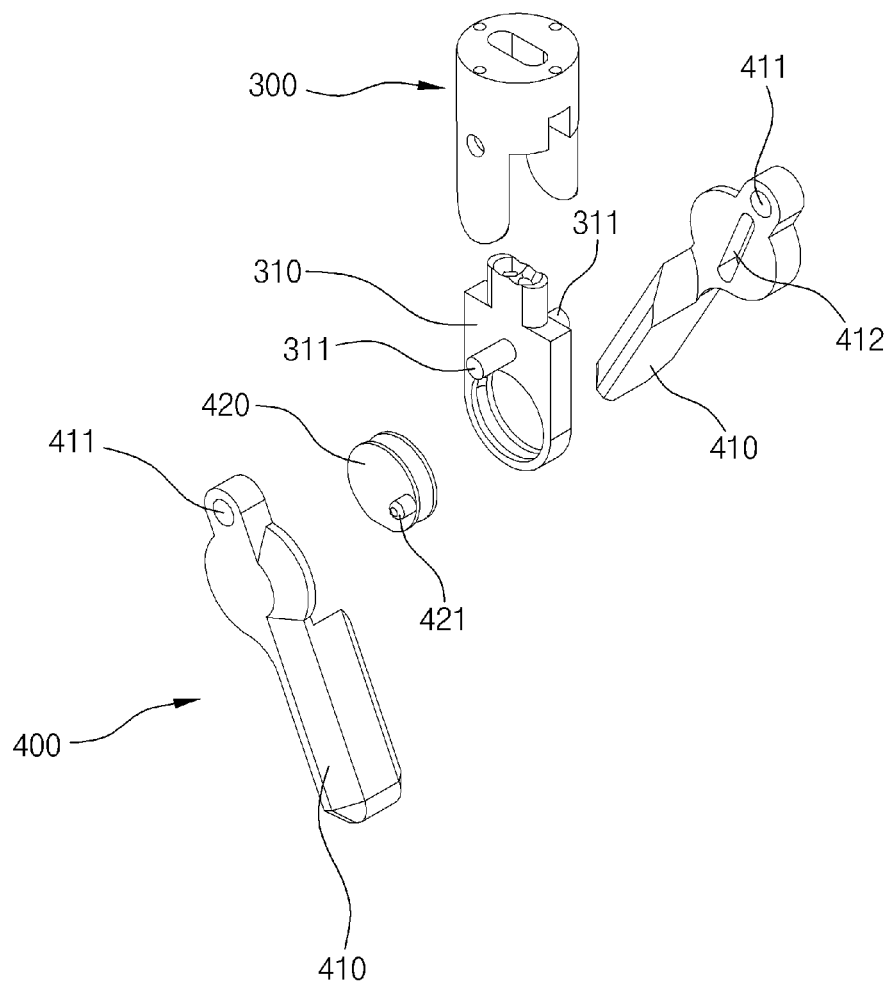
FIGS. 11 and 12 are exploded perspective views illustrating the forceps of FIG. 10.
Figure 12:
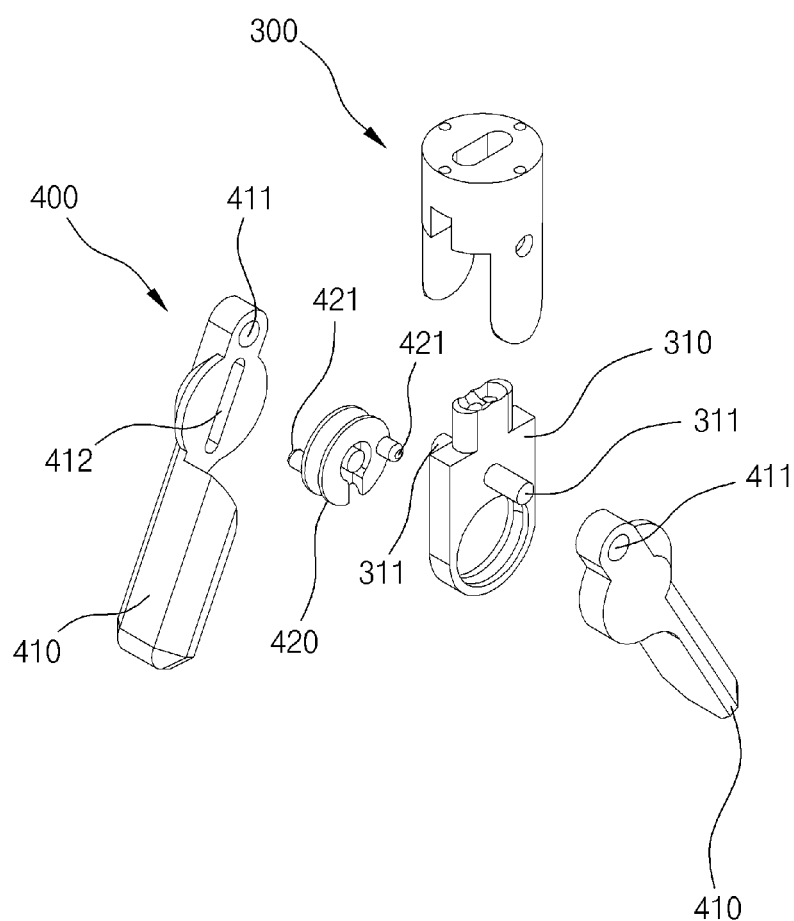
Figure 13:
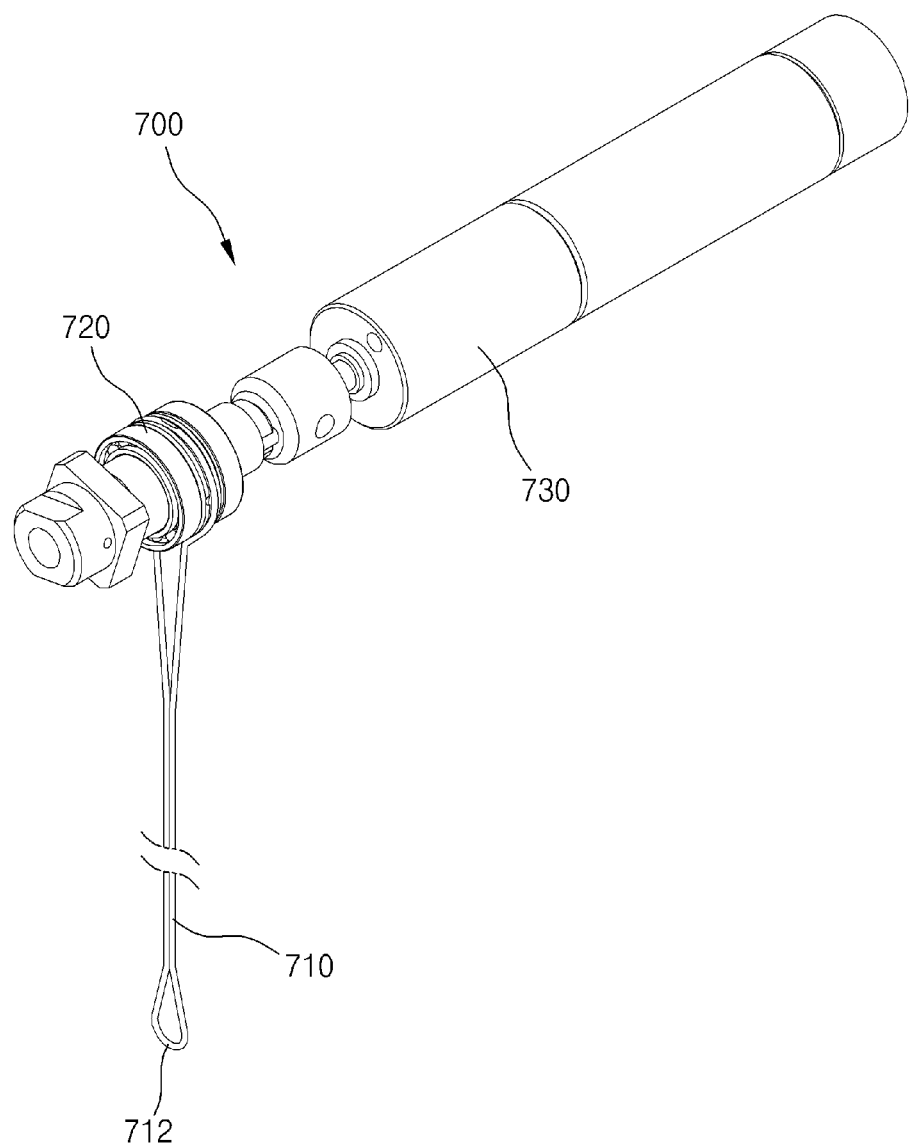
FIG. 13 is a perspective view showing the details of a forceps-driving unit of a laparoscopic surgical instrument having a small diameter shaft in accordance with an embodiment of the present invention.

Referring to FIGS. 11 to 13, the forceps 400 include a pair of forcep jaws 410 attached to the body 310, which is connected with the head 300, a driving roller 420, and a forceps-driving unit 700.

The forceps jaw 410 is formed with a piercing pivot insertion opening 411 on the top portion thereof and a guide slit 412 elongated along an inclination inside the jaw 410. The driving roller 420 is rotatably installed on the body 310 and formed with driving pins 421 eccentrically protruded on both sides. The forceps-driving unit 700 includes a forceps-driving wire 710, a forceps-driving roller 720, and a forceps-driving motor 730.

For the assembly sequence of the forceps 400 structured as above, the folded portion 712 of the forceps-driving wire 710 inserted via the through-hole in the head 300 is wound on the exterior circumference of the driving roller 420. The driving roller 420 is rotatably connected with the body 310. The forcep jaws 410 on both sides are coupled with each other in such a fashion that the driving pins 421 of the driving roller 420 assembled on the body 310 are inserted into the guide slits 412, respectively. Finally, the body 310 and the forcep jaws 410 are inserted into the head 300, and a fixing shaft 311 is inserted into the body 310 and the pivot insertion openings 411 of the forcep jaws 410.

Figure 17:
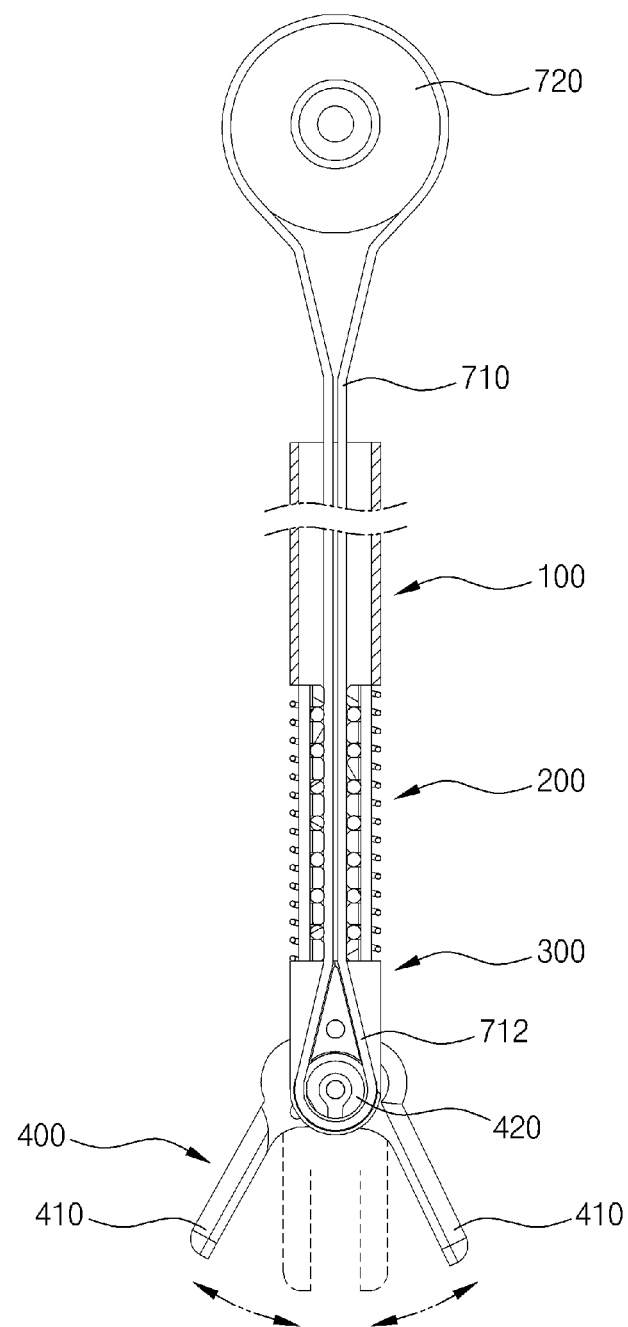
FIG. 17 is a perspective view showing the operating state of the forceps in the laparoscopic surgical instrument having a small diameter shaft in accordance with an embodiment of the present invention.

Referring to FIGS. 13 and 17, the forceps 400 configured as above are actuated by the forceps-driving unit 700, which includes the forceps-driving wire 710, the forceps-driving roller 720, and the forceps-driving motor 730.

The forceps-driving wire 710 is folded into two halves in such a fashion that a folded portion 712 passes through the hollow opening portion of the shaft 100 and the flexible joint 200 and surrounds the exterior circumference of the driving roller 420 engaged on the body 310 of the head 300. Here, the opposite end of the forceps-driving wire 710 is connected with the forceps-driving roller 720 installed on the proximal top end of the shaft 100. The forceps-driving roller 720 can be turned by the forceps-driving motor 730, thereby making the forceps-driving wire 710 rotate in one direction.

In the exemplary embodiment of the present invention, the laparoscopic surgical instrument having a small diameter shaft can be used as being connected with a slave robot (not shown) of a robot-assisted laparoscopic surgery (not shown). However, the present invention is not limited thereto, and can be used as a laparoscopic surgical instrument with a separated manipulating means attached thereto for an individually operated and manipulated laparoscopic surgery.

The operations of the laparoscopic surgical instrument having a small diameter shaft formed with the above mentioned figures in accordance with the present invention will be described more in detail.

Referring to FIGS. 8 and 14, the longitudinal-driving motor 530 connected with the longitudinal-driving roller 520 needs to be rotated in order to turn the head 300 in the longitudinal direction by bending the flexible joint 200 in the longitudinal direction. The longitudinal-driving roller 520 connected with the longitudinal-driving motor 530 can turn at an angle of certain number of degrees in one direction by the turning power of the longitudinal-driving motor 530. When the longitudinal-driving roller 520 turns in the clockwise direction, the left side of the longitudinal-driving wire 510 wound around the longitudinal-driving roller 520 can be wound around the longitudinal-driving roller 520 and the right side thereof can be unwound from the longitudinal-driving roller 520. When the left side of the longitudinal-driving wire 510 contracts and the right side of the longitudinal-driving wire 510 extends in this manner, the flexible joint 200 is pressed to reduce the space between the head 300, connected with the left side of the longitudinal-driving wire 510, and the shaft 100. The small rings 210 and the large rings 220 forming the flexible joint 200 are bent by downward pressure from above while drawing a circle. When the flexible joint 200 is bent while drawing a circle, the head 300 rotates to the left side of the longitudinal direction around the shaft 100.

In order to turn the head 300 in the right side of the longitudinal direction, the longitudinal-driving motor 530 needs to rotate in the counterclockwise direction, contrary to the above motion. When the longitudinal-driving motor 530 rotates in the counter-clockwise direction, the longitudinal-driving roller 520 connected with the longitudinal-driving motor 530 turns in the counterclockwise direction, and the left side of the longitudinal-driving wire 510 wound around the longitudinal-driving roller 520 extends and the right side of the longitudinal-driving wire 510 contracts. When the length of the longitudinal-driving wire 510 changes based on the longitudinal-driving roller as above, the flexible joint 200 is bent to the right side of the longitudinal direction around the shaft 100 by the longitudinal-driving wire 510 and the head 300 turns to the right side.

The longitudinal-driving unit 500 enabling the flexible joint 200 to bend in the longitudinal direction can rotate the head 300 up and down by 90 degrees in the longitudinal direction.

Referring to FIGS. 9 and 15, the transverse-driving motor 630 of the transverse-driving unit 600 is operated in order to bend the flexible joint 200 in the transverse direction. When the transverse-driving motor 630 rotates, the transverse-driving roller 620 can turn at an angle of a certain number of degrees in one direction and the transverse-driving wire 610 is wound around the transverse-driving roller 620. When the transverse-driving roller 620 turns in the clockwise direction, the left side of the transverse-driving wire 610 can be wound around the transverse-driving roller 620 and the right side of the transverse-driving wire 610 can be unwound. Consequently, the left side of the transverse-driving wire 610 can contract and the right side of the transverse-driving wire 610 can extend around the transverse-driving roller 620, and the flexible joint 200 is pressed to reduce in the left direction between the head 300, connected with the left terminal portion 611 of the transverse-driving wire 610, and the shaft 100. At this time, the small rings 210 and the large rings 220 forming the flexible joint 200 are bent in the left direction by downwards pressure while drawing a circle. The flexible joint 200 is bent in the left direction as above and the head 300 rotates to the left side of the transverse direction around the shaft 100.

In order to turn the head 300 to the right side of the transverse direction, the transverse-driving motor 630 is rotated in the counterclockwise direction contrary to the above motion. When the transverse-driving motor 630 rotates in the counterclockwise direction, the left side of the transverse-driving wire 610 wound around the transverse-driving roller 620 extends and the right side of the transverse-driving wire 610 contracts. When the length of the transverse-driving wire 610 changes, the flexible joint 200 is bent to the right side and the head 300 can turn to the right side of the transverse direction around the shaft 100.

The flexible joint 200 bending as above can rotate the head 300 by 90 degrees in the left/right side of the transverse direction around the extended axis of the shaft.

Figure 16:
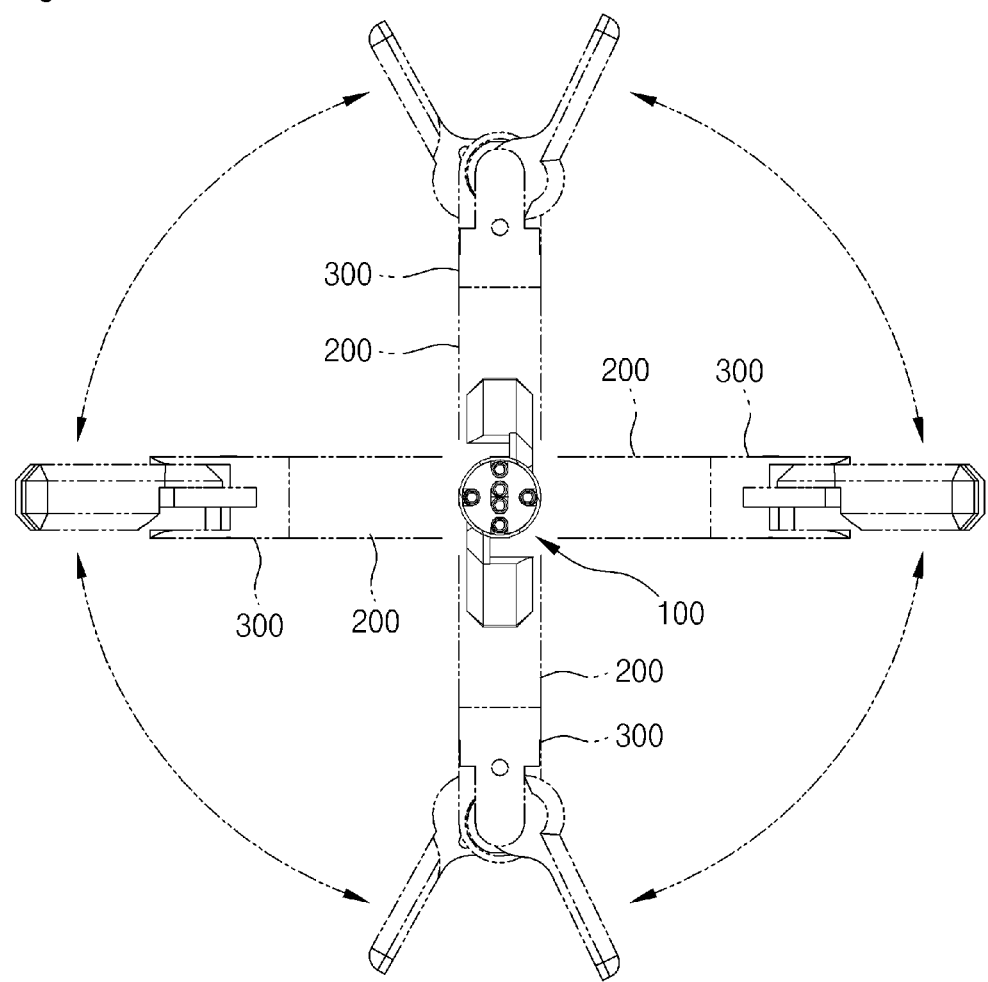
FIG. 16 is a top plan view showing the rotating state of the head around the shaft in the laparoscopic surgical instrument having a small diameter shaft in accordance with an embodiment of the present invention.

Referring to FIG. 16, the flexible joint 200 bending in both longitudinal and transverse directions within 90 degrees, respectively, can be used together with the longitudinal-driving unit 500 and the transverse-driving unit 600, and the head 300 can rotate 360 degrees in all directions around the shaft 100 when the longitudinal-driving unit 500 and the transverse-driving unit 600 are operated at the same time.

Referring to FIG. 17, the forceps 400 formed on the head 300 can be actuated via turning of the forceps-driving roller 720 by rotating the forceps-driving motor 730. When the forceps-driving roller 720 turns, one side of the forceps-driving wire 710 is wound around the forceps-driving roller 720 and the other side of the forceps-driving wire 710 is unwound. At this time, the folded portion 712 of the forceps-driving wire 710 rotates around the driving roller 420 and the driving roller 420 turns in the rotating direction of the forceps-driving wire 710. When the forceps-driving roller 720 turns in the clockwise direction by using the forceps-driving motor 730, the forceps-driving wire 710 rotates in the clockwise direction together with the forceps-driving roller 720. At this time, the driving roller 420 rotatably connected with the folded portion 712 of the forceps-driving wire 710 can rotate in the clockwise direction together with the forceps-driving wire 710. When the driving roller 420 turns in the clockwise direction as above, both forcep jaws 410 in which the guide slits 412 are connected with the driving pins 421 can be closed up until the opposing sides come into contact with each other by the rotation of the driving roller 420.

In order to open the forcep jaws 410, the forceps-driving roller 720 is turned in the counterclockwise direction. When the forceps-driving roller 720 turns in the counter-clockwise direction, the forceps-driving wire 710 also rotates in the counterclockwise direction and the driving roller 420 connected with the forceps-driving wire 710 also rotates in the counterclockwise direction, and both the forcep jaws 410, in which the guide slits 412 are connected with the driving pins 421 of the driving roller 420, are opened by moving in both directions.

As set forth above, it is to be appreciated that those skilled in the art can make substitutions, or change or modify the embodiments into various forms without departing from the scope and spirit of the present invention. Accordingly, the foregoing embodiments should be regarded as illustrative rather than limiting. The scope of the present invention is not defined by the detailed description as set forth above but by the accompanying claims of the invention. It should also be understood that all alterations or modifications derived from the definitions and scopes of the claims and their equivalents fall within the scope of the invention.

The invention claimed is:

1. A laparoscopic surgical instrument including a shaft and a head having a distal end to which a variety of surgical instruments are attached, the laparoscopic surgical instrument comprising:
  a flexible joint installed between the shaft and the head;
  a longitudinal-driving unit including a longitudinal-driving wire connected with both longitudinal ends of the head and a longitudinal-driving roller turning the longitudinal-driving wire, wherein the longitudinal-driving unit turns the flexible joint in a longitudinal direction;
  a transverse-driving unit including a transverse-driving wire connected with both transverse ends of the head and a transverse-driving roller turning the transverse-driving wire, wherein the transverse-driving unit turns the flexible joint in a transverse direction; and
  forceps included or connected to the head, wherein the forceps include:
  a couple of forcep jaws separated to top and bottom sides and rotatably attached to the head at a pivot;
  a distal driving roller configured to rotate the forceps; and
  a forceps-driving unit configured to actuate the distal driving roller to turn the forceps, wherein each of the forcep jaws has a linearly elongated guide slit formed on an inside thereof that is elongated along an inclination away from the pivot, and
  wherein the distal driving roller is rotatably coupled with a body connected with the head and has driving pins eccentrically protruded on both sides, each of the driving pins connected with the guide slit of each of the forcep jaws,
  wherein the shaft has a small diameter, and
  wherein the driving pins move in different directions in the guide slit according to a direction of rotation of the driving roller, and both forcep jaws are closed up until opposing sides come into contact with each other or are opened by moving in both directions.

2. The laparoscopic surgical instrument in accordance with claim 1, wherein the longitudinal-driving wire of the longitudinal-driving unit is partially wound on the longitudinal-driving roller, the transverse-driving wire of the transverse-driving unit is partially wound on the transverse-driving roller, and both ends of the longitudinal-driving wire and the transverse-driving wire are inserted into the shaft and extend through an outside of the flexible joint so as to be connected with the head.

3. The laparoscopic surgical instrument in accordance with claim 1, wherein the flexible joint includes a plurality of rings arranged in a row.

4. The laparoscopic surgical instrument in accordance with claim 3, wherein the plurality of rings comprises first rings and second rings larger than first rings alternately arranged in a row.

5. The laparoscopic surgical instrument in accordance with claim 4, wherein the first rings and the second rings larger than first rings are made of elastic material.

6. The laparoscopic surgical instrument in accordance with claim 4, wherein each of the second rings larger than first rings have guide grooves on outer exterior circumferential portions thereof that the longitudinal-driving wire and the transverse-driving wire are linearly inserted into the guide grooves.

7. The laparoscopic surgical instrument in accordance with claim 6, wherein the guide grooves are arranged in the outer exterior circumferential portions of the second rings larger than first rings at 90 degree intervals.

8. The laparoscopic surgical instrument in accordance with claim 3, further comprising an outer cover attached to an outside of the flexible joint so as to prevent the longitudinal-driving wire and the transverse-driving wire from moving out of the guide grooves of the second rings larger than first rings.

9. The laparoscopic surgical instrument in accordance with claim 8, wherein the instrument comprises a steel wire that is repeatedly wound into a coil shape with an equal diameter.

10. The laparoscopic surgical instrument in accordance with claim 1, wherein the forceps-driving unit includes:
  a forceps-driving wire inserted through the shaft, the flexible joint and a through-hole of the head, and having a folded portion wound on an exterior circumference of the distal driving roller;
  a forceps-driving roller provided on an upper portion of the shaft that a terminal portion of the forceps-driving wire is wound thereon; and
  a forceps-driving motor turning the forceps-driving roller.

* * * * *